United States Patent [19]

Rosenberg

[11] 4,332,893

[45] Jun. 1, 1982

[54] PROCESS FOR THE PRODUCTION OF AN INSULIN-PRODUCING CELL LINE OF PANCREATIC BETA CELLS

[76] Inventor: Ralph A. Rosenberg, 124 Johnson St., Apt. 1-B, Highland Park, N.J. 08904

[21] Appl. No.: 159,450

[22] Filed: Jun. 13, 1980

[51] Int. Cl.$^3$ .................. C12N 5/02; C12P 21/00; C12N 15/00

[52] U.S. Cl. ........................ 435/68; 435/235; 435/240; 435/241; 435/172; 435/948

[58] Field of Search ............... 435/68, 172, 241, 238, 435/948, 235, 239, 240, 236

[56] References Cited

U.S. PATENT DOCUMENTS 3,093,831  6/1963  Jordan ........................... 3/1
4,082,613  4/1978  Thirumalacher et al. ...... 435/172 X

FOREIGN PATENT DOCUMENTS 467  7/1979  World Intellectual Prop .... 435/172

OTHER PUBLICATIONS

Magun et al., *Chemical Abstracts,* 87:51327r, 313 (1977).
Altaner et al., Carcinogenesis by RNA Sarcoma Viruses, Virology 40 118–134, (1970).
Balduzzi, Cooperative Transformation Studies with Temperature Sensitive Mutants . . . J. Virology 18:332–342, (Apr. 1976).
Biquard et al., Characteristics of a Conditional Mutant of Rous Sarcoma Virus . . . Virology 47:444–455, (1972).
Graf et al., Differential Expression of Transformation of Rat and Chicken Cells Infected with an Avian Sarcoma Virus ts Mutant, Virology 56:369–374, (1973).
Hayward et al., Detection of Avian Tumor Virus RNA . . . J. Virology 11:157–167, (Feb. 1973).
Holtzer et al., Effect of Oncogenic Virus on Muscle Differentiation, Proc. Nat. Acad. Sa. U.S.A. 72:4051–4055, (1975).
Kobayashi et al., Induction of DNA Synthesis in Terminally Differentiated Myotubes . . . Proc. Nat. Acad. Sci: USA 75:5501–5505, (1978).
Kostianovsky et al., Monolayer Cell Culture of Adult Rat Islets of Langerhans, Diabetologia 10:337–344, (1974).
Lacy et al., Method for the Isolation of Intact Islets of Langerhans from The Rat Pancreas, Diabetes 16:35–39, (Jan. 1967).
Morgan et al., Immunoassay of Insulin, Diabetes 12:115–126, (Mar.–Apr. 1963).
Neisor et al., Establishment of Rat Pancreatic Endocrine Cell Lines by Infection with Simian Virus 40, Biochem. J. 178:559–568, (1979).
Ono et al., Long-Term Culture of Pancreatic Islet Cells, In Vitro 15:95–102, (1979).
Sun et al., Insulin Secretion from a Continuously Subcultivatable Isolate Derived from Foetal Pancreata Beta Cells, Biochem. & Biophys. Res. Comm. 79:195–289, (1977).
Weiss et al., Induction of Avian Tumor Viruses in Normal Cells . . . Virology 46:920–938, (1971).
Wyke, Temperature Sensitive Mutants of Avian Sarcoma Viruses, Biochim et Biophys. Acta, (1975).

*Primary Examiner*—Esther M. Kepplinger
*Attorney, Agent, or Firm*—Sixbey, Friedman & Leedom

[57] ABSTRACT

A process for producing an insulin-producing conditionally transformed pancreatic cell line is provided. The process of the present invention comprises the steps of preparing and culturing a population of insulin-producing pancreatic beta cells, preparing and culturing a suitable strain of Rous sarcoma virus containing a temperature sensitive lesion in the viral transforming or sarc gene, and infecting the insulin-producing pancreatic cells with the temperature sensitive virus. The infected pancreatic cells are conditionally transformed by the temperature-sensitive virus to provide an insulin-producing system especially suited for both in vitro and in vivo application. Methods for evaluating the safety of the system for application in vivo are also disclosed.

16 Claims, No Drawings

PROCESS FOR THE PRODUCTION OF AN INSULIN-PRODUCING CELL LINE OF PANCREATIC BETA CELLS

TECHNICAL FIELD

The present invention relates generally to the production of insulin by living cell systems. In particular, the present invention relates to a process for producing an insulin-producing cell line comprised of pancreatic beta cells conditionally transformed by a mutant strain of temperature sensitive Rous sarcoma virus.

BACKGROUND ART

The therapeutic value of insulin and, in particular, human insulin in treating diabetic patients has long been appreciated. The primary commercial source of insulin for therapeutic application, however, has been that prepared from bovine or porcine pancreas. Because of such factors as the immunological differences between human and animal insulin which may result in the formation of anti-insulin antibodies after prolonged use in humans and the often uncertain availability of bovine and porcine pancreas, efforts to produce significant quantities of insulin from human pancreas have increased. To date, efforts to produce human insulin have concentrated on either the chemical synthesis or the biological cultivation of insulin-producing pancreatic cells. The chemical synthesis of human insulin involves several very complex steps and has proved to be quite costly on a large scale, particularly in comparison to the methods currently utilized for the commercial production of bovine and porcine insulin. The known biological methods for producing insulin are promising but are not without their limitations and disadvantages. Available and suggested methods are, for the most part, limited to insulin production under in vitro conditions. It would be highly desirable to provide a method of supplying a continuous, long term in vivo source of insulin to a diabetic patient. However, those methods which have potential in vivo as well as in vitro application have fallen short of expectations. In addition, some of the known in vitro biological methods are not suitable for the production of insulin on a large scale.

Current biological methods for producing human insulin have focused on cellular transformation, either of the growth rate, morphology and structure, of the cell function or some combination of these. For example, in U.S. Pat. No. 4,082,613, Thirumalachar et al. teach the extraction of the functional genomic material, that portion of the deoxyribonucleic acid (DNA) which controls the production of insulin, from human or other mammalian pancreatic beta epitheliod cells. This DNA fraction is then used to transform functionally a population of fungal cells to produce insulin. While the aforementioned process may be suitable for the in vitro production of insulin on a large scale, the application of the process is limited to in vitro conditions, and does not obviate the need for separately administering a therapeutic dose of insulin to the diabetic patient.

A method for producing insulin which has both in vitro and in vivo application was reported by Neisor et al. in Biochem. J., 178, 559–68 (1979), in which a primary culture of rat pancreatic endocrine cells was morphologically transformed by simian virus 40 (SV 40). The method reported therein, while promising, suffers nonetheless from some significant drawbacks regarding its application to humans, including the unconditional nature of the transformation, which makes control of the expression of the virus extremely difficult, and the potentially biohazardous effects associated with the SV 40 virus in humans.

The prior art has thus failed to disclose a method of producing an insulin-producing cell line comprising a primary culture of conditionally transformed insulin-producing pancreatic cells which may be utilized either in vitro as an exogenous insulin supply or in vivo in an individual patient to provide a long term endogenous source of insulin.

DISCLOSURE OF INVENTION

Therefore, it is a primary object of the present invention to provide a process for producing a conditionally transformed line of insulin-producing cells comprising the steps of isolating and subculturing a population of insulin-producing pancreatic beta cells, growing a culture of a mutant strain of Rous sarcoma virus containing a temperature sensitive lesion in the viral transforming gene, infecting the beta cells with the temperature sensitive virus to produce a conditionally transformed line of insulin-producing beta cells and culturing the conditionally transformed cell line. It is another object of the present invention to provide a process for producing a line of insulin-producing pancreatic cells which may be utilized either in vitro or in vivo as a source of insulin whereby a primary culture of pancreatic cells is conditionally transformed by a temperature-sensitive mutant strain of Rous sarcoma virus.

It is an additional object of the present invention to provide a process for preparing a line of insulin-producing pancreatic cells for the in vitro or in vivo production of insulin, capable of generating a theoretically infinite number of cells with a long term insulin-producing capacity.

It is yet another object of the present invention to provide safeguards whereby the conditionally transformed insulin-producing cell line produced according to the present process may be made as free from biohazardous effects as possible prior to the in vivo use of the cell line.

In accordance with the aforementioned objects, a process is provided for producing a line of insulin-producing pancreatic cells whereby a primary culture of pancreatic beta cells is conditionally transformed by a temperature sensitive mutant strain of Rous sarcoma virus. The process of the present invention includes the steps of isolating and subculturing insulin-producing pancreatic beta cells and growing up a stock of a suitable mutant strain of Rous sarcoma virus containing a temperature sensitive lesion on the transforming gene of the virus. The pancreatic beta cell population is then infected with the virion-containing fraction of the virus culture to produce a line of conditionally transformed insulin-producing pancreatic beta cells, which are then subcultured to produce the desired cell population. The conditionally transformed insulin-producing cell line may be readily stored for future use or may be utilized as either an in vitro or an in vivo supply of insulin.

Other objects and advantages of the present invention will become apparent from a study of the following Best Mode for Carrying Out the Invention and the appended claims.

BEST MODE FOR CARRYING OUT THE INVENTION

The process for producing of the insulin-producing pancreatic cell line of the present invention may be conveniently subdivided into three parts: the isolation and culturing of a population of pancreatic cells capable of producing insulin; the preparation and culturing of a suitable temperature sensitive mutant strain of Rous sarcoma virus; and the infection of the pancreatic cells by the temperature sensitive Rous sarcoma virus to produce the conditional transformation thereof. An additional part of the following section discusses the in vitro and in vivo application of the cell line produced according to the present process.

I. PREPARATION OF A SUITABLE CULTURE OF INSULIN-PRODUCING PANCREATIC BETA CELLS

The process described herein may be applied to obtain a culture of human, bovine or porcine insulin-producing pancreatic cells; however, the preferred culture is one of human pancreatic cells. Once the species with which it is desired to work has been selected, normal pancreas must be obtained. It is preferred to use pancreas obtained by sterile dissection from human, bovine or porcine fetuses. Since the individual islets of Langerhans which contain the insulin-producing beta cells are scattered and constitute only a small percentage of the pancreas, techniques used for their isolation must be able to separate effectively the islets from the rest of the pancreas. Many such methods are known to those skilled in the art. One effective method for isolating the islets is the sedimentation method reported by Lacy et al. in Diabetes 16, 35–39 (1967), as modified by Sun et al. in Biochem. and Biophys. Research Comm. 79, 185–89 (1977). Using aseptic conditions, under which instruments are sterilized and solutions are autoclaved or sterilized by passage through a Millipore filter with a pore size no greater than 0.45 micron, the dissected pancreatic tissue is dressed and perfused by multiple puncture with Hanks' balanced salt solution. With scissors or a scalpel the tissue is then minced into pieces that are about 1 cubic millimeter in size. These pieces of tissue are digested for about 20 to 30 minutes at about 32° to 39° C., preferably at 37° C., in a solution of collagenase and hyaluronidase. It is preferred to use Type IV collagenase at a concentration of about 3.75 mg/ml of pancreatic tissue and hyaluronidase at a concentration of about 2.5 mg/ml of pancreatic tissue from Worthington Biochemical, Freehold, N.Y. Partial purification of the isolated islets from the pancreatic acinar cells may be achieved by washing with Hanks' solution and decanting. The remaining solids are then digested with a 0.25% trypsin solution for about 5 to 10 minutes at about 32° to 39° C., preferably 37° C., and prepared in a calcium and magnesium-free phosphate buffered saline solution. (Kostianovsky et al., Diabetologia 10, 337–44 (1974)).

Alternatively, the minced pancreatic tissue may be placed in a collagenase solution at a concentration of 10 to 15 mg of enzyme per ml Hanks' solution and incubated in a closed container at 32° to 39° C., preferably 37° C., with continuous stirring provided by a magnetic stirrer. After incubation the mixture is diluted with about 15 to 25 ml of Hanks' solution, preferably in a sterile conical graduated cylinder to facilitate settling. Intact islets should settle to the bottom of the cylinder within about one minute, after which time the supernatant is removed, preferably with a sterile needle, and discarded. The sediment containing the islets is resuspended in Hanks' solution, allowed to settle for about 30 seconds and the supernatant removed and discarded. This step is repeated at least eight times, using cold Hanks' solution for the last four suspensions. Examination of the sediment at this point with a dissecting microscope should reveal intact islets without evidence of necrosis or degeneration.

Further dispersal of the isolated islets to produce a population of single cells is highly desirable to achieve maximum efficiency of virus infection. Production of the optimum single cell population may be accomplished by one of the methods known to those skilled in the art. The method reported by Ono et al. in In Vitro, 15, 95–102 (1979), is particularly suitable for preparing pancreatic cells for subsequent viral infection. The islet of Langerhans-containing sediment collected by one of the methods described hereinabove is dissociated into single cells by treatment with 0.02% ethylenediaminetetraacetate (EDTA) in a calcium ion and magnesium ion free (CMF) balanced salt solution for about 5 minutes and collected by centrifugation. The islets are then transferred to a flask of CMF balanced salt solution containing about 4 ml of 1000 PU per ml Dispase-II, a proteolytic enzyme obtained from the culture filtrate of *Bacillus polymyxa*. Dissociation is achieved by gentle stirring at about 32° to 39° C., preferably 37° C., for about 15 minutes, after which time the cell clumps are allowed to settle and the supernatant removed. Repetition of the Dispase digestion step at least three additional times assures a maximum yield of single cells. It may be desirable, though not critical, at this point to calculate the viability of the cells by one the many conventionally used methods.

The single cell suspension thus obtained should be rich in insulin-producing pancreatic beta cells. These cells are preferably then pelleted by low speed centrifugation and the resulting pellet suspended in a nutrient medium. A nutrient medium particularly preferred for this purpose is that known in the art as Medium 199 supplemented with about 10% by weight heat inactivated calf serum, about 400 I.U. per ml penicillin, about 200 micrograms per ml streptomycin, about 14 mM per ml sodium bicarbonate, and about 17 mM per ml glucose. The cells are then counted by conventional means and seeded on standard tissue culture plates at a preferred density of about $10^6$ cells per 50 mm diameter plate. It is preferred that infection with the transforming virus be carried out immediately after plating since uninfected beta cells lose their capacity to produce insulin with serial subculturing.

II. PREPARATION OF THE TRANSFORMING VIRUS STOCKS

Heretofore, efforts to transform insulin-producing pancreatic beta cells with viruses have focused on the use of viruses which unconditionally transformed the cells so that there was no way in which the transformation process, once started, could be controlled. By employing a viral strain in which a mutation in the transforming gene has caused the expression of this gene to be sensitive to the environmental temperature, the transformation function of the virus can be controlled by adjusting the temperature. At its permissive temperature the mutant viral transforming gene is stable and can function to transform the morphology or growth rate of an infected host cell. At its nonpermissive temperature, the mutant viral transforming gene is inactivated and incapable of transformation. The specific permissive and nonpermissive temperatures are influenced by such factors as species of the host cell and the particular mutant viral strain containing the temperature sensitive lesion. Since human body temperature is typically within the nonpermissive temperature ranges for the viral strains preferred for use in the present process, these viral strains are especially suitable for the in vivo application of the insulin producing cell line produced as disclosed herein.

Two strains of Rous sarcoma virus (RSV) are preferred for use in the conditional transformation process of the present invention. The first is known in the art as ts-sarc-SR-RSV-D mutant FU-19, isolated by Biquard and Vigier as reported in Virol, 47, 444–55 (1972), and the second is one of the ts-sarc mutants of the Bryan strain of Rous sarcoma virus isolated by Balduzzi as reported in J. Virol., 18, 332–43 (1976). The first mentioned Rous sarcoma virus belongs to subgroup D and contains a protein in the viral envelope which enhances its efficiency in transforming mammalian cells, including human cells. The Bryan strain of the virus has a defect in the envelope (env) gene and therefore must be engineered to infect mammalian cells by one of the methods known in the art, such as by fusion of the viral and cellular membranes with inactivated Sendai virus, or by pseudotype formation whereby the env-defective Bryan virus would acquire the envelope protein from a nontransforming helper RNA tumor virus of subgroup C or D, such as Rous associated virus (RAV)-50, during coinfection of chick embryo fibroblasts, thus permitting the infection of mammalian cells. Both virus strains contain a temperature sensitive lesion in the transforming (sarc) gene which results in the expression of the transforming gene being dependent on the environmental temperature as discussed hereinabove. Although either virus may be used in the transforming process of the present invention, each presents certain advantages and disadvantages. For example, no helper virus is required to assure infection with the ts-sarc-SR-RSV-D virus, while the defective env gene in the Byran strain of RSV makes it unlikely that other cells in the human or animal would be infected in the rare event of a release of the virus from conditionally transformed beta cells implanted in vivo.

Once a strain of Rous sarcoma virus is selected, virus stocks may be grown up by one of a number of methods known to those skilled in the art. The preferred method is described herein. These steps should be performed under aseptic techniques as described in Section I so that sterilized reagents, glassware and instruments are used at all times.

Chick embryo fibroblasts, type C/O, are suspended in a nutrient medium and seeded to a density of about 2.0 to $3.0 \times 10^6$ to each 100 mm diameter tissue culture plate. The preferred nutrient medium for this purpose contains about 40 parts of Medium 199 to about 5 parts of tryptose phosphate broth to about 2.5 parts of calf serum to about 1 part of about 2.8% sodium bicarbonate. This medium is supplemented with about 400 I.U. penicillin and about 200 micrograms streptomycin sulfate per milliliter of medium. Infection, preferably at a multiplicity of infection of about 0.2, of the chick embryo fibroblasts with the virus of choice should occur within about four hours after the cells have been plated. The infected cells are then incubated at 32° to 39° C., preferably 37° C., in an incubator with a humidified atmosphere of about 95% air and 5% $CO_2$. The cultures should be examined daily for the spread of transformation. In addition, it is important to change the nutrient medium at least every 48 hours. In about 5 to 7 days, the cultures should be confluently transformed and harvesting of the supernatant, which contains the desired virions or infective viral particles, may begin. However, if a different nutrient medium other than the Medium 199 composition described above is used for culturing the virus-infected chick embryo fibroblasts, the last change of medium prior to harvesting the supernatant should be to the Medium 199 composition described above. The harvested supernatants may be stored at about $-60°$ C. to $-70°$ C. for at least 6 months until ready for use.

III. INFECTION AND CONDITIONAL TRANSFORMATION OF INSULIN-PRODUCING PANCREATIC CELLS WITH THE TEMPERATURE SENSITIVE-VIRUS PREPARATION

The infection step should preferably take place within about four hours after the pancreatic cells prepared according to the process described in Section I above have been plated. It may first be necessary, however, to adjust the pH of the virion-containing supernatant obtained as a result of the steps described in Section II. This supernatant may have an acidity higher than that which is optimal for the culture of the pancreatic cells, and the virion-containing supernatant is generally sufficiently acid to kill at least a portion of the pancreatic cells. Therefore, adjustment of the pH of the supernatant to a preferred pH of about 7.2 to 7.8 is preferably accomplished with sterile buffered 1.0 M Hepes solution. Once the pH has been adjusted appropriately, the pancreatic cells are infected with the selected virus strain at a multiplicity of infection of about 10.

The virus-infected pancreatic cells are then cultured at the permissive temperature which is that temperature at which the transforming gene is expressed. As discussed hereinabove, the permissive temperature can vary but is generally in the range of about 33° to 34° C. for a mammalian host cell. The infected cells are maintained in the culture medium, which is the supplemented Medium 199 composition used to grow the virus stocks in Section II. This medium should be changed at least every two days.

The conditionally transformed insulin-producing pancreatic beta cells thus obtained may be stored for several years by perfusing them with the above described medium supplemented with 20% dimethylsulfoxide and 20% serum and freezing them in a liquid nitrogen refrigerator.

It is advantageous at this point, as well as prior to storage, to ascertain the insulin-producing capacity of the transformed virus-infected pancreatic cells. First the incubation temperature of the infected cells must be shifted to the nonpermissive temperature, which is that temperature at which the mutant sarc gene is inactivated and transformation will cease. As with the permissive temperature, the non-permissive temperature can vary, but is usually in the range of about 37° to 39° C. for a mammalian host cell. Incubation at this temperature should continue for at least about 60 hours. The capacity of the transformed cells to produce insulin may then be determined by one of many methods conventionally used for this purpose. However, an adaptation of the procedure of Sun et al. in Biochem. and Biophys.

Res. Comm., 79, 185–89 (1977), is preferred for use in the process of the present invention.

After incubation of the cells for at least about 60 hours at the nonpermissive temperature, the cells are washed at least three times and resuspended in a serum-free culture medium which has the same composition as the Medium 199 composition described in Section I above, but without the calf serum. After a period of at least about 24 hours, the transformed cells may be subjected to a glucose challenge. This is accomplished by replacing the culture medium with the same serum-free medium to which 300 mg glucose per 100 ml medium has been added and incubating the cells at the nonpermissive temperature for at least about 24 hours. A control culture of transformed cells in medium to which no glucose has been added should be incubated with the glucose-containing culture. In addition, the insulin-producing capacity of pancreatic cells produced according to the process set forth in Section I, but which have not been infected with one of the Rous sarcoma virus strains prepared according to the process set forth in Section II, should also be ascertained at this time. The same glucose challenge procedure should be followed for two cultures of the nontransformed cells as is followed with the transformed cells. After the incubation period, samples taken from the culture medium are subjected to one of the standard procedures for insulin determination. A particularly preferred procedure is a radioimmunoassay for insulin, such as that described by Morgan et al. in Diabetes, 12, 115–26 (1963). While both the glucose challenged transformed and nontransformed cells should show a positive radioimmunoassay for insulin, a quantitative determination of the insulin production of both types of cells should show the production of a greater amount of insulin by the transformed cells over the same period of time.

Since it is generally necessary to be able to subculture a cell line such as that produced according to the present invention, a determination of the success of subculturing the transformed cells at the permissive temperature is highly desirable. To make this determination, the cells are disaggregated by conventional methods, such as by incubation with trypsin or collagenase, after which the suspension is centrifuged and the cells resuspended in fresh Medium 199 containing serum of the composition described hereinabove. After the cells are replated, cell viability is determined. Microscopic examination of the cells should indicate that the transformed morphology and growth rate have been retained after replating. A more precise determination of cell viability should also be made by ascertaining the extent to which radioactively labeled thymidine is incorporated into the deoxyribonucleic acid (DNA) of the replated cells as compared to the radioactive thymidine incorporation into the DNA of an uninfected pancreatic cell control, which procedure is well known to those skilled in the art.

IV. APPLICATION OF THE INSULIN-PRODUCING CELL LINE OF THE PRESENT INVENTION

To maintain the conditionally transformed pancreatic cell line of the present invention as an in vitro or exogenous source of insulin, the cells are cultured as described hereinabove at the permissive temperature until a desirably large population is obtained, at which point the culture medium is replaced with a high glucose medium, preferably one that contains at least about 300 mg glucose per 100 ml of culture medium. After incubation with the high glucose medium for at least about 24 hours, the medium may be harvested for insulin at regular intervals, such as about every 24 hours. Of course the cells must be fed fresh high glucose medium after the old medium is harvested to maintain the viability of the insulin-producing cell line. Although it is not known at this point precisely how long the conditionally transformed cells will continue to produce insulin under the conditions described herein, the capacity of conditionally transformed pancreatic cells to produce significant quantities of insulin should far surpass the 80 day period during which cultured nontransformed pancreatic cells have been found to produce insulin.

It is anticipated that one application of the insulin-producing cell line of the present invention would be as an in vivo or endogenous insulin supply in a diabetic patient, preferably in the form of an implant. A form for such an implant is suggested in U.S. Pat. No. 3,093,831. Enclosure of the conditionally transformed insulin-producing cell line of the present invention within a physiologically inert dialysis membrane having a pore size sufficiently large to permit the passage of insulin molecules having a molecular weight of about 6000 from the implant but small enough to prevent the passage of antibodies having a molecular weight of about 140,000 into the implant or the passage of the viruses out of the implant would be a preferred in vivo system. Utilization of the insulin-producing cell line produced according to the process of the present invention as an in vivo insulin supply is not without its potential problems to the human or other animal in which it is implanted. However, some modifications of the procedures described herein may be made which should minimize or eliminate any potential problems.

Since the Rous Sarcoma virus belongs the group of ribonucleic acid (RNA) tumor viruses, it possesses oncogenic potential. Consequently, proliferation of the implanted cells due to what is known in the art as "leakiness", that is failure of the ts-sarc gene product to be completely inactivated, or due to reversion of the ts-sarc gene to wild type by mutation could possibly lead to tumor formation in the human or animal in which the cell line of the present invention was implanted. Release of the virus from the conditionally transformed pancreatic cells of the in vivo system, while a less likely eventuality, could pose similar problems. It is therefore, desirable to determine the oncogenic potential of the conditionally transformed cell line prior to in vivo application. A short-range test of oncogenicity may be performed to ascertain the in vivo safety of the conditionally transformed cell line. The conditionally transformed pancreatic beta cells are implanted subcutaneously into nonimmunocompetent (nude) mice which are then observed for tumor development for at least four months following injection of the conditionally transformed cells. A dialysis membrane is not required since the mice preferred for use in this test are not immunocompetent. It may be necessary to use diabetic mice since nondiabetic mice are likely to die from insulin overdose prior to the development of any tumors. The absence of tumor formation in the mice during this period is indicative of the unlikelihood of tumor formation in the event of release of the conditionally transformed cell line from an in vivo implant.

A more stringent and, thus, preferred test of the safety of the implant for in vivo and, ultimately, human use, however, is a long term study of diabetic animals carrying the implanted cell line of the present invention for at least a period of two years. A major advantage of the proposed cell line is that it is possible to ascertain whether any tumors which arise are of conditionally transformed cellular implant or viral etiology either by a virus rescue experiment or by nucleic acid hybridization. The procedure described by Altaner and Temin in Virol. 40, 118–34 (1970) is preferred for the virus rescue experiment. The tumor cells are irradiated with at least 5000 Rads of X-rays (100 kv, 8 mA). These irradiated cells are mixed with chick embryo fibroblasts and fused with inactivated Sendai virus. Analysis of the supernatant produced will reveal a virus biologically like that used to produce the implant, that is the virus in the supernatant will contain the ts-sarc gene and belong to the same subgroup as that used to conditionally transform the pancreatic cells. If the tumor is large enough and contains sufficient deoxyribonucleic acid (DNA), a nucleic acid hybridization test will also demonstrate whether the tumor is of viral or conditionally transformed cellular etiology. Of the techniques for this test known in the art, that of Hayward and Hanafusa, described in J. Virol. 11, 157–67 (1973) is preferred. Briefly, this technique detects the viral genetic information which, as a result either of the initial infection of the pancreatic cells, or by infection of other host cells by virus released from the implanted, conditionally transformed beta cells, has been transcribed into DNA and integrated into the cells' chromosomal DNA.

Release of the virus, if it did occur, would most likely be due to exposure to X-irradiation and subsequent rupture of the dialysis membrane, if that is the manner in which the cell line is implanted. It is possible to determine the minimum X-ray dosage required to cause induction of the Rous sarcoma virus strain from the conditionally transformed pancreatic cells in vitro to ascertain whether induction of the virus by X-rays is a potential problem. A precise determination of the maximum tolerable levels of X-irradiation which could be administered without causing the complication alluded to above would have to be determined by an appropriate in vivo study. An adaptation of the procedure described by Weiss et al. in Virol., 46, 920–38 (1971), is preferred to determine this X-ray dose.

Cultures of ts-sarc-RSV transformed insulin-producing pancreatic cells are irradiated with 0, 500, 1000, 2000 and 5000 rads, respectively, placed in culture dishes and covered with a layer of soft agar-containing nutrient medium, such as the Medium 199 composition described hereinabove. A feeder layer of chick embryo fibroblasts is placed over the solidified agar and a layer of nutrient medium on top of the feeder layer. If the dose of radiation has caused release of the virus from the pancreatic cells, transformed foci are observed in the chick embryo fibroblasts and a positive assay for reverse transcriptase activity, a test conventionally used to detect the presence of viruses by those skilled in the art, is obtained.

The aforementioned release of the virus by X-rays is only a potentially serious problem if the transforming virus used is the strain of Rous sarcoma virus known as ts-sarc-SR-RSV-D. The Bryan strain, which can also be used in the present process, contains a defective envelope gene, and, as discussed hereinabove, cannot readily penetrate mammalian cells in the absence of complementation of the defective env function by pseudotype formation during the growth of the virus stocks. Therefore, the ts-sarc-SR-RSV-D strain is probably preferable for use in the in vitro system described herein, while a Byran strain, such as ts-sarc-Bryan-RSV+RAV-50, is likely to be safer for use in the in vivo system described herein.

It is further anticipated that the problems which could arise from the oncogenic potential of the Rous sarcoma virus strain ts-sarc-SR-RSV-D would be diminished by using infected pancreatic cells which have reverted to the nontransformed phenotype at the permissive temperature. To isolate complete or partial revertants, conditionally transformed pancreatic cells produced as described hereinabove and shown to be hormonally active are dispersed through the use of an enzyme such as trypsin or collagenase and diluted for seeding in the wells of standard culture plates in a nutrient medium, such as Eagle's medium without serum. Each well should preferably contain only one cell. The plated cells are then incubated at the permissive temperature (33° to 34° C.) for at least about 24 hours and examined to identify cells which appear morphologically normal and evidence no morphological transformation during growth. These revertant insulin-producing pancreatic cells are then used in place of the cells exhibiting transforming activity at the permissive temperature as described hereinabove. The preferred use of a population of revertant cells would be in the proposed in vivo insulin producing system. It should be noted, however, that the revertant cells still contain both viral genetic information and the ts-sarc gene product, and, therefore, the oncogenic biohazard potential must be determined by the safety evaluation procedures outlined hereinabove prior to their in vivo application.

Most temperature sensitive mutants of Rous sarcoma virus are "leaky", that is the mutant gene product is not completely inactivated at the nonpermissive temperature. Therefore, the possible safety risks of the in vivo system due to "leakiness" may be minimized by transforming bovine or porcine pancreatic cells rather than human pancreatic cells to produce the insulin-producing cell line. If the conditionally transformed bovine or porcine cell line thus produced is implanted in a human, such as in a dialysis membrane as described above, and if due to "leakiness" of the ts-sarc gene function, the conditionally transformed cells should proliferate, release of the cells from the membrane, such as by rupture of the membrane due to trauma, will lead to rejection of the foreign bovine or porcine cells by the human host before any oncogenic potential is realized.

INDUSTRIAL APPLICABILITY

The process of the present invention will find its primary application in the production of an insulin-producing system. This system may be utilized either as an in vitro source of insulin which is then administered to diabetic patients by conventional means, or alternatively, the insulin-producing system of the present invention may be implanted in vivo to provide a continuous endogenous supply of insulin.

It is apparent that many modifications and variations of this invention as hereinabove set forth may be made without departing from the spirit and scope thereof.

I claim:
1. A process for producing an insulin-producing pancreatic cell line by conditionally transforming pancreatic cells with a temperature sensitive mutant strain of Rous sarcoma virus, said process comprising the steps of

(a) selectively isolating insulin-producing beta cells from a pancreas and culturing said insulin-producing cells to produce a homogeneous population thereof;

(b) growing a culture of a mutant strain of Rous sarcoma virus in a manner to produce a supernatant portion which contains the virion of said mutant strain of said virus, said mutant strain of virus containing in the transforming gene thereof a temperature sensitive lesion which causes said transforming gene to be expressed at a permissive environmental temperature and to be inactivated at a non-permissive environmental temperature;

(c) harvesting the virion-containing supernatant portion of said mutant virus culture including said temperature sensitive transforming gene and infecting said insulin-producing pancreatic cells with said virion of said mutant virus so that the expression of said temperature sensitive transforming gene causes the conditional transformation of said insulin-producing pancreatic cells at said permissive temperature;

(d) culturing the resulting infected insulin-producing pancreatic cells at the permissive temperature for the expression of the temperature sensitive transforming gene of said mutant virus strain in said insulin-producing pancreatic cells for a time sufficient to cause the conditional transformation of said insulin-producing pancreatic cells by said temperature sensitive transforming gene and to produce a desirably large population of said insulin-producing pancreatic cells; and (e) shifting the temperature of the culture produced in step (d) to the nonpermissive temperature for the inactivation of the temperature sensitive transforming gene of said mutant virus strain in said insulin-producing pancreatic cells for a time sufficient to cause said conditionally transformed insulin-producing pancreatic cells to revert to a non-transformed state and to produce insulin.

2. The process described in claim 1, wherein said insulin-producing pancreatic cells are obtained from a human pancreas.

3. The process described in claim 1, wherein said insulin-producing pancreatic cells are obtained from a bovine pancreas.

4. The process described in claim 1, wherein said insulin-producing pancreatic cells are obtained from a porcine pancreas.

5. The process described in claim 1, wherein said mutant strain of Rous sarcoma virus is selected from the group consisting of the viral strains ts-sarc-SR-RSV-D and ts-sarc-Bryan-RSV.

6. The process described in claim 5, wherein said mutant strain of Rous sarcoma virus comprises the strain ts-sarc-SR-RSV-D mutant FU-19.

7. The process described in claim 5, wherein said mutant strain of Rous sarcoma virus comprises the strain ts-sarc-Bryan-RSV.

8. The process described in claim 7, further including the step of fusing the membrane of said mutant viral strain ts-sarc-Bryan-RSV and the membrane of said insulin-producing cells with inactivated Sendai virus.

9. The process described in claim 7, further including the step of adding a nontransforming helper RNA tumor virus of subgroup C or D during step (b).

10. The process described in claim 9, wherein said nontransforming helper RNA tumor virus is Rous associated virus (RAV)-50.

11. The process described in claim 1, further including the steps of:

(a) enzymatically dispersing said conditionally transformed insulin-producing pancreatic cells;

(b) diluting said dispersed cells with nutrient medium and plating a single cell in each of the wells of a standard tissue culture plate;

(c) incubating said plated cells at the permissive temperature for the expression of the temperature sensitive transforming gene of said mutant virus strain in said insulin-producing pancreatic cells for at least about 24 hours; and (d) selecting those of said insulin-producing pancreatic cells showing no evidence of morphological transformation and culturing said morphologically normal pancreatic cells to obtain an insulin-producing cell population.

12. A process for producing an insulin-producing cell line of pancreatic cells by conditionally transforming pancreatic cells with a temperature sensitive strain of Rous sarcoma virus, said process comprising the steps of (a) selectively isolating insulin-producing beta cells from a human pancreas to produce a suspension of single cells rich in insulin producing beta cells, pelleting said cells by low speed centrifugation, suspending the pellet thus formed in nutrient medium and plating said cells;

(b) growing a culture of a mutant strain of Rous sarcoma virus including a temperature sensitive lesion in the transforming gene thereof which causes the transforming gene to be expressed at a permissive environmental temperature and to be inactivated at a nonpermissive environmental temperature by infecting chick embryo fibroblasts with said mutant strain and incubating the infected fibroblasts in a nutrient medium in a manner to produce a supernatant portion which contains the virion of said mutant strain of Rous sarcoma virus for a time sufficient to confluently transform said culture;

(c) harvesting said supernatant portion of said culture and adjusting the pH of said supernatant to a pH in the range of about 7.2 to 7.8;

(d) infecting the pancreatic cells obtained in step (a) with the virion-containing supernatant obtained in step (c);

(e) culturing said infected pancreatic cells at the permissive temperature for the expression of the temperature sensitive transforming gene of said mutant virus strain in insulin-producing pancreatic beta cells for a time sufficient to cause said insulin-producing pancreatic cells to be conditionally transformed by the expression of said temperature sensitive transforming gene;

(f) culturing in a culture medium the conditionally transformed insulin-producing pancreatic cells at the permissive temperature for a time sufficient to produce a desirably large population of said insulin-producing pancreatic cells; and (g) replacing the culture medium containing the conditionally transformed insulin-producing pancreatic cells with a culture medium containing glucose, incubating said cells in the glucose medium at the nonpermissive temperature for the inactivation of the temperature sensitive transforming gene of said mutant virus strain in said insulin-producing pancreatic cells for a time sufficient to cause said conditionally transformed insulin-producing pancreatic cells to revert to a nontransformed state and to produce insulin, and harvesting the insulin-produced by said cells in said nontransformed state from said glucose medium.

13. The process described in claim 12, wherein said mutant strain of Rous sarcoma virus is selected from the group consisting of the viral strains ts-sarc-SR-RSV-D and ts-sarc-Bryan-RSV.

14. The process described in claim 13, wherein said mutant strain of Rous sarcoma virus comprises the strain ts-sarc-SR-RSV-D mutant FU-19.

15. The process described in claim 13, wherein said mutant strain of Rous sarcoma virus comprises the strain ts-sarc-Bryan-RSV.

16. The process described in claim 12, further including the steps of:
    (a) enzymatically dispersing said conditionally transformed insulin-producing pancreatic cells;
    (b) diluting said dispersed cells with nutrient medium and plating a single cell in each of the wells of a standard tissue culture plate;
    (c) incubating said plated cells at the permissive temperature for the expression of the temperature sensitive transforming gene of said mutant virus strain in said insulin-producing pancreatic cells for at least about 24 hours; and
    (d) selecting those of said insulin-producing pancreatic cells showing no evidence of morphological transformation and culturing said morphologically normal pancreatic cells to obtain an insulin-producing cell population.

* * * * *